United States Patent [19]

Loth et al.

[11] Patent Number: 4,536,217

[45] Date of Patent: Aug. 20, 1985

[54] ABSORBING COVER FOR WOUNDS AND THE METHOD FOR MANUFACTURING THEREOF

[75] Inventors: Fritz Loth; Horst Dautzenberg, both of Tetlow, German Democratic Rep.; Jiří Štamberg; Jan Peška, both of Prague, Czechoslovakia; Dieter Bertram; Herbert Lettau, both of Leipzig, German Democratic Rep.

[73] Assignees: Ceskoslovenska akademie ved of Praha, Prague, Czechoslovakia; Akademie der Wissenschaften der DDR, Berlin, German Democratic Rep.

[21] Appl. No.: 537,151

[22] Filed: Sep. 28, 1983

Related U.S. Application Data

[63] Continuation of Ser. No. 286,250, Jul. 23, 1981, abandoned.

[30] Foreign Application Priority Data

Jul. 30, 1980 [CS] Czechoslovakia .................... 5332-80
Jul. 30, 1980 [CS] Czechoslovakia .................... 5330-80

[51] Int. Cl.³ .............................................. C08C 1/24
[52] U.S. Cl. .................................... 106/122; 106/164; 536/57; 536/87
[58] Field of Search ...................... 106/164, 122, 168; 536/57, 87

[56] References Cited

U.S. PATENT DOCUMENTS

| | | | |
|---|---|---|---|
| 3,652,540 | 3/1972 | Determann et al. | 536/87 |
| 3,852,224 | 12/1974 | Bridgeford | 106/168 |
| 4,055,510 | 10/1977 | Peska et al. | 106/164 |
| 4,110,529 | 8/1978 | Stoy | 528/491 |
| 4,281,063 | 7/1981 | Tsao et al. | 536/56 |

*Primary Examiner*—Theodore Morris
*Attorney, Agent, or Firm*—Murray Schaffer

[57] ABSTRACT

The invention pertains to the absorbing dressing for wounds, which consists of spherical particles of regenerated cellulose of the size 0.05–0.5 mm (preferably 0.05–0.3 mm) and a macroporous structure characterized by the cyclohexane regain of the dry material at least 0.2 ml/g. The dressing is prepared from the regenerated cellulose swollen with water by replacement with organic solvents and the subsequent drying of the product swollen with the said solvent. The porous structure of the dressing warrants that it can absorb excretions of the wound in the amount 1.5 to 5 g water per g of solids; the grainy macrostructure remains preserved during the absorption so that the material applied on the wound in the form of a powder in the layer 2–5 mm thick, in particular 2–3 mm thick, can be without difficulties and almost without pain rinsed away with water.

13 Claims, No Drawings

ABSORBING COVER FOR WOUNDS AND THE METHOD FOR MANUFACTURING THEREOF

This is a continuation of U.S. Ser. No.: 286,250, Filed: 7/23/81, now abandoned.

The invention pertains to an absorbing cover for wounds, which serves for coating of heavily oozing infectious wounds as well as of affected areas in disorders of skin and tissue, and also to the method for manufacturing thereof.

In addition to powders successfully applied in the pharmaceutical practice for many years, they proved recently suitable in particular composite powders, consisting of compounds with a bactericidal or bacteriostatic activity and a basic component, as talc, lactose, starch, and the like, and also natural and synthetic polymers and copolymers, among others chitin and chitosan (MIT Sea Grant Rep. MITSG 1978; Proc. Int. Conference Chitin/Chitosan 1977, p. 296–305), collagen (Belg. Pat. No. 856,603), crosslinked dextrans (e.g. S. Jacobson et al., Scand. J. Plast. Reconstr. Surg. 10 (1976), p. 65–72), cellulose derivatives (e.g. Dutch Pat. No. 6,807,540), polypropylene (Swiss Pat. No. 472,894), soft polyurethane foams (e.g. H. Bohmert, Med. Welt 28 (1977) p. 826–831; S. Kiene, Dt. Gesundheit-Wesen 34 (1979), p. 2010–2014; W. Kothe et al., Medizin aktuell 10 (1979), p. 452–453), copolymers of cellulose and acrylic acid (Brit. Pat. No. 1,141,271), and also copolymers of vinyl esters with unsaturated carboxylic acids (DOS No. 2,653,135). They are applied either as such or as the carriers with active compounds, e.g. of bactericidal or bacteriostatic activity, namely with antibiotics, sulfonamides and antimycotics. Similar dressings for wounds are recommended also in the treatment of Acne vulgaris and Psoriasis.

Among the materials mainly used in the absence of an active compound, the crosslinked dextrans and soft polyurethane foams have proven suitable, the latter in particular as so called "synthografts". These nontoxic, biologically inert materials compatible with tissues have a relatively rough porous structure, which enables reception of water in the amount corresponding to a multiple of their own weight. If applied on oozing infectious wounds, they influence their purgation and restrict infection in an excellent way, while removing exudate, bacteria, fungi, inflammatory mediators, toxins and their decomposition products from the surface of wound. Because these materials may take up proteins, including the cleavage products of the system fibrin-fibrinogen, the formation of scab is prevented. On the other hand, granulation and epithelisation are supported.

Certain shortcomings have to be considered with crosslinked dextrans and soft polyurethane foams, which stand against their positive effects and limit their application. Thus, the absorption of water or exudate proceeds in crosslinked dextrans relatively slowly. They swell during absorption to a gellike layer which decreased the permeation of gas.

Dressings from soft polyurethane foams must be cut according to the shape of wound, otherwise they adher insufficiently and the purgation of wound is strongly reduced. They should not extend to the healthy surroundings of the wound. This kind of dressings needs to be changed very often, i.e. very twelve hours if possible, otherwise the granulations grow into the material and can be separated only with painful bleeding over a large area.

The aim of the invention is a dressing for wounds which exhibits positive effects of crosslinked dextrans and soft polyurethane foams, while overcoming their above mentioned shortcomings, and in particular the provision of a nontoxic dressing compatible with tissues, which may be adapted to the shape of wound or the respective part of skin and tissue, in addition to the clean coating and protection from infection, removes exudate from heavily oozing wounds rapidly and regardfully of a patient, in addition to the exudate, removes also bacteria, fungi, toxins, proteins, and inlammation mediators, does not swell to a gellike layer by absorption of water or exudate, may be sterilized and additionally sterilized, supports granulation and epithelisation.

As we have suggested in Acta Polymerica 30 (1979), p. 734, the properties of some cellulose materials promise to meet the aforesaid requirements. The aim of the invention is to develop a dressing for wounds based on cellulose, which is biologically inert, i.e. nontoxic and compatible with tissues, and exhibits the properties mentioned above, and to work out a simple method for preparation of such cover which may be realized in the technical scale and requires only low technical and economical investment in comparison with the known laboratory procedures. The fundamental physical properties, which may serve for evaluation of these materials, are the porosity in dry state measured as the cyclohexane regain (ml of cyclohexane per g of solids) and the water regain in equilibrium (ml of water per g of solids).

The direct drying of porous cellulose materials in a water-wetted state leads to virtually nonporous products as a consequence of the larger or smaller breakdown of pores. The original porosity is neither maintained while water is removed by azeotropic distillation with benzene, xylene or tetrachloromethane. The breakdown of pores is fairly prevented if water is removed by the gradual replacement of solvents in the sequence of decreasing polarity (Cell. Chem. Technol. 21 (1978) 419–428).

However, the replacement of solvents in the stated sequence is rather unfavourable and time consuming. In addition, this method requires very expensive separation and recovery of solvents. Another possible drying procedure maintaining the pores is a critical point drying method. The multistep exchange of solvents is necessary also in this method and further disadvantage consists in the elevated pressure required.

The pores can be preserved in a considerable measure during freeze drying under certain conditions, e.g. by rapid cooling with liquid nitrogen and sublimation of water at very low temperature, but the cooling technique necessary for this procedure is very expensive.

The objective of the invention is an absorbing dressing for wounds, which consists of spherical particles of regenerated cellulose of diameter 0.05 to 0.5 mm, particularly 0.05 to 0.3 mm, having a macroporous structure characterized by the porosity in dry state, corresponding to the cyclohexane regain at least 0.2 ml per g of solids, and which is prepared from the water-swollen regenerated beaded cellulose by action of organic solvents and the subsequent drying of the product swollen with the solvent.

Further objective of the invention is a method for preparation of the aforesaid dressing for wounds from the water-swollen regenerated beaded cellulose by means of replacement of solvents, wherein a single solvent or a single mixture of solvents is employed as the liquid remover water. Drying of the material swollen with the given solvent proceeds in the step following the removing of water and gives the product a high and controllable porosity in the dry state. The fraction of particles with the size of 0.05 to 0.5 mm is then separated from the product and freed of mechanical impurities. The cellulose particles may be advantageously additionally impregnated with therapeutically active compounds in the dissolved form and then packed into containers and sterilized by gamma rays.

It has been surprisingly found, that the porosity of cellulose materials can be preserved during drying also without replacement of the whole series of organic solvents with the gradually decreasing polarity, but that the aim of the invention can be met by allowing a solvent, or a mixture of solvents, which sufficiently removes water, to flow over the cellulose materials in a sufficient amount or in a closed cycle with drying. It also appeared that water may be removed from the system while maintaining the porosity, also by distillation, if suitable liquids were used, which were limitedly miscible with water and regained more than 5% of water, i.e. the suitable solvents or solvent mixtures consisting of a solvent miscible with water without limitation and a solvent immiscible with water. In both cases, water is removed from pores of the cellulose materials and replaced by an organic solvent or a mixture of solvents, which during its subsequent removal prevents the pores from breakdown. The portion of pores preserved and, consequently, the defined porosity of the final product may be controlled in a broad region by a suitable selection of solvents and of drying methods.

According to the invented method, the main amount of water is first removed from the wet cellulose material, e.g. by centrifugation, suction, or by single or multiple washing with always the same volumes of an organic solvent limitedly or unlimitedly miscible with water, or of the mixture of organic solvents miscible and nonmiscible with water.

One of the methods according to the invention consists in placing the pretreated cellulose materials into a suitable exchange column or other vessel, where the organic solvent limitedly or unlimitedly miscible with water, or a mixture of solvents miscible and immiscible with water, is allowed to flow over the materials at ambient temperature or at temperature which is lower than the boiling temperature of solvent. The composition of solvent mixture has to be chosen for this process in such a way, that water retained in the cellulose materials does not cause the phase separation. The employed solvent, or the mixture of solvents, in the amount corresponding to 2-200 fold volume of the cellulose material, may be forced through the column by pressure or suction. The solvent or the solvent mixture enriched with water may be freed of water by distillation or by sorption, e.g. on suitable molecular sieves, and again introduced into the column with cellulose. After water has been completely replaced by the solvent or the mixture of solvents, the latter is removed from the cellulose materials, e.g. by evaporation under normal pressure or in vacuum at the boiling temperature or by a stream of inert gas, air or superheated vapor.

In another method of performing the invention, the cellulose materials preferably with the main portion of retained water removed, are transferred into a suitable distillation vessel, e.g. a kettle equipped with a stirrer, drum drier, or the flask of a rotation evaporator. Then, the solvent partially miscible with water, or the mixture of organic solvents miscible and nonmiscible with water, is added in the amount corresponding to 2-200 fold volume of the wet cellulose materials and the residual water in the cellulose materials is removed from the system cellulose/solvent by distillation. If the mixture of solvents is used, the amounts of both components has to be chosen in such a way, that water retained in the cellulose materials does not cause the phase separation during distillation. After the separation of phases in the distillate, the water-immiscible phase is advantageously returned to the cellulose materials wetted by solvents and the final drying is carried out first after the main part of water-miscible solvent has been removed from the cellulose materials. The evaporation of the residual solvent is carried out again in vacuum or at normal pressure.

Alcohols with one to three carbon atoms in the molecule, preferably ethanol or 2-propanol, or ketones, preferably acetone, are used as the water-miscible organic solvents, 1-butanol, 2-butanol or 3-butanone are preferably used as the organic solvents partly miscible with water, and aromatic hydrocarbons and their derivatives, preferably benzene, toluene, xylene or chlorobenzene, or cycloaliphatic hydrocarbons, preferably cyclohexane or methylcyclohexane, are used as the water-immiscible organic solvents.

The classification of product is carried out, for example, by screening, e.g. on shaking, oscillating or vibrating screens. Mechanical admixtures may be removed in air separators or magnetically in drum separators. The suitable packing material represent containers of glass, plastics or metal.

In the manufacturing of the absorbing dressing for wounds according to the invention, regenerated cellulose may be advantageously used, which was produced according to the U.S. Pat. No. 4,055,510.

The porous structure warrants that the dressing can absorb excretions of the wound in the amount 1.5 to 5 g water per g of solids; the grainy macrostructure remains preserved during the absorption so that the material applied on the wound in the form of a powder in the layer 2-5 mm thick, in particular 2-3 mm thick, can be without difficulties and almost without pain rinsed away with water.

While an aqueous exudate is absorbed mainly into macropores of cellulose particles, the capillary forces, which act in the interparticle space, remove from the surface of wound also bacteria, fungi, toxins, proteins and inflammatory mediators. The absorption of exudate occurs more rapidly than with crosslinked dextrans, because the cellulose particles need not swell during this sorption.

The invention is further illustrated in details by examples, where the product is directly applicable as a dressing to cover wounds.

EXAMPLE 1

Wet spherical cellulose particles of average diameter 450 μm, prepared according to the U.S. Pat. No. 4,055,510, were freed of the main amount of retained water by suction and twofold washing always with the same amount of acetone corresponding to the volume of wet cellulose. The product (20 g) pretreated in such a way was placed in an exchange column and washed with another acetone, which was continuously dropped on the cellulose particles. The solvent enriched with water was led through another column containing 10 g of molecular sieve. Acetone freed of water in this column was again led on the cellulose material. The re-pumping of acetone was continued for 2 hours, which corresponded to about 3 l of passing acetone. The retained acetone was then removed from the virtually anhydrous cellulose particles by suction and its residue by evaporation in vacuum. The material was screened on a screen with nominal aperture of 0.3 mm. The measure of porosity in the dry state was the cyclohexane regain of 0.3 ml/g. The water regain on swelling to equilibrium was determined by the centrifugation method (cf. Cell. Chem. Technol., 21 §1978) 419–428) and amounted to 1.9 ml/g. The product, which was washed with the same amount of acetone, but without drying, exhibited the cyclohexane regain 0.05 ml/g and the water regain 1.1 ml/g. The latter values correspond approximately to the product which was dried directly from water.

EXAMPLE 2

The cellulose particles, freed of the main portion of retained water similarly as in Example 1, were transferred in the amount of 20 g into the extraction thimble of a Soxhlet apparatus. Another Soxhlet extractor was placed below the extraction vessel and its thimble was filled with 10 g of molecular sieve. The distilling flask was charged with 500 ml of acetone, which was evaporated and condensed to sprinkle the cellulose particles. Acetone flowed through cellulose and was enriched with water. Then it flowed through the molecular sieves, where it was dried, and was returned into the distilling flask. After fivetimes passing of acetone through the Soxhlet, the cellulose particles were dried by suction and the residual acetone was removed by evaporation in vacuum. The product obtained in this way exhibited the cyclohexane regain 0.3 ml/g and the equilibrium water regain 2.0 ml/g.

EXAMPLE 3

The cellulose particles, freed of the main portion of retained water by suction on a sintered-glass filter, were freed of water in the amount of 20 g by means of 2-propanol analogously as in Example 2. The cyclohexane regain in dry cellulose particles was 0.9 ml/g and the equilibrium water regain 3.2 ml/g.

EXAMPLE 4

The cellulose particles freed of the main portion of retained water as in Example 1, but using 96% denatured ethanol as the washing liquid, were further freed of water and dried in the amount of 20 g analogously as in Example 2 by means of 96% denatured ethanol. The obtained product had the cyclohexane regain 0.5 ml/g and the equilibrium water regain 2.4 ml/g.

EXAMPLE 5

The cellulose particles freed of the main amount of retained water as in Example 1, but by means of 2-butanone as the washing liquid, were further freed of water and dried in the amount of 20 g analogously as in Example 2 by means of 2-butanone. The obtained cellulose particles had the cyclohexane regain 0.35 ml/g and the equilibrium water regain 2.0 ml/g.

EXAMPLE 6

The cellulose particles, freed of the main amount of retained water by suction on a sintered-glass filter, were further freed of water and dried in the amount of 20 g analogously as in Example 1 by means of ethanol and cyclohexane in the volume ratio 5:1. The obtained cellulose particles had the cyclohexane regain 0.55 ml/g and the equilibrium water regain 2.4 ml/g.

EXAMPLE 7

The cellulose particles freed of the main portion of retained water as in Example 1, but by means of 96% denatured ethanol as the washing liquid, were transferred in the amount of 100 g into the distilling flask of a rotation evaporator together with the mixture consisting of 100 ml of ethanol and 500 ml of benzene. Water and ethanol were distilled together with benzene at the normal pressure. The remaining solvent was distilled off in the vacuum of water-jet pump. The cellulose particles dried in this way exhibited the cyclohexane regain 1.2 ml/g and the equilibrium water regain 3.5 ml/g.

EXAMPLE 8

The cellulose particles, freed of the main amount of retained water as in Example 1, but by means of 96% denatured ethanol as the washing liquid, were transferred in the amount of 100 g into the distilling flask of a rotation evaporator together with the mixture consisting of 100 ml of ethanol and 500 ml of cyclohexane. Water and ethanol were then distilled off together with cyclohexane. The remaining solvent was removed by distillation in the vacuum of water-jet pump. The cyclohexane regain of cellulose particles was 2.2 ml/g and the equilibrium water regain 4.5 ml/g.

EXAMPLE 9

The cellulose particles, freed of the main amount of retained water by suction on a sintered-glass filter, were transferred in the amount of 100 g into the distilling flask of a rotation evaporator together with 500 ml of the mixture consisting of 2-propanol and cyclohexane in the volume ratio 1:5. Water and 2-propanol were then distilled off together with cyclohexane. The remaining solvent was removed by distillation in the vacuum of water-jet pump. The cyclohexane regain of the cellulose particles amounted 1.6 ml/g and the equilibrium water regain 4.0 ml/g.

EXAMPLE 10

The particles of beaded cellulose of diameter 0.5 mm were freed of the main portion of retained water as in Example 1, but using 2-butanol as the washing liquid. Then they were transferred in the amount of 100 g into the distilling flask of a rotation evaporator together with 500 ml of 2-butanol, freed of water by distillation, and dried. The obtained product had the cyclohexane regain 1 ml/g and the equilibrium water regain 3.3 ml/g.

EXAMPLE 11

The cellulose particles, freed of the main amount of retained water as in Example 1, but using 96% denatured ethanol as the washing liquid, were transferred in the amount of 100 g into the distilling flask of a rotation evaporator together with 100 ml of ethanol and 100 ml of cyclohexane. A part of the solvent mixture was then distilled off and the nonaqueous phase separating from the distillate was returned into the distilling flask in 50 ml portions. This procedure was repeated 10 times more. After that, water did not separate from the distillate as the second phase. The remaining solvent retained in cellulose particles was removed in an air oven at 80° C. The obtained product had the cyclohexane regain 1.7 ml/g and the equilibrium water regain 4.0 ml/g.

EXAMPLE 12

The dry beaded cellulose (100 g), manufactured analogously as in Example 4, was classified on a shaking or oscillating screen, the fraction of particle size 0.05 to 0.3 mm was freed of mechanical admixtures in an air separator or magnetically in a drum separator, air-tightly sealed in a container of glass, plastics or metal, and sterilized by gamma rays.

EXAMPLE 13

The beaded cellulose (10 g), according to Example 12, was successively washed with 500 ml of 1% ethanolic solution of bacitracin and 500 ml of diethylether and dried in vacuum at ambient temperature to the constant weight. The antibiotics was absorbed in the porous beaded cellulose in the amount of 45 mg per g of solids, i.e. of 2300 international units per g.

We claim:

1. A powder dressing for wounds comprising spherical particles of water swollen regenerated cellulose beads wherein the water had first been replaced by an organic solvent, the solvent sequentially removed and the beads dried, said particles having a diameter of between 0.05 to 0.5 mm and a macroporous structure characterized by a porosity in the dry state corresponding to the cyclohexane regain of at least 0.2 ml/g of the dry material.

2. The dressing according to claim 1 wherein the particles have a diameter of 0.05 to 0.3 mm.

3. A method for forming a powder dressing for wounds which consists of the sequence of steps of water swelling a mass of regenerated cellulose beads, contacting said water swollen beads with one of an organic solvent solution selected from the group consisting of (a) a water miscible, (b) a partly water miscible, or (c) a mixture of a water miscible and a water immiscible organic solvent, and capable of absorbing at least 5% water to form a mixture of solvent and water, removing the water from said mixture until all the water in said mixture and said beads is replaced with solvent and said solvent maintains said beads swollen, removing said solvent and drying said beads, and separating from said dried beads those particles having a diameter of at least 0.05 mm and a macroporous structure characterized by a porosity in the dry state corresponding to the cyclohexane regain of at least 0.2 ml/g of the dry material.

4. The method according to claim 3 wherein the water swollen beads is contacted with 2 to 20 volumes of said organic solvent per one volume of said swollen beads at a temperature between the ambient temperature and the boiling temperature of the solvent.

5. The method according to claim 3 wherein the step of removing the water from the solvent-water mixture is effected by distillation of said solvent and water and the separation of the water from said distillate.

6. The method according to claim 3 wherein the step of removing the water from the solvent-water mixture is effected by elution of said mixture and the separation of the water from the elute.

7. The method according to claim 5 wherein after removal of the water from the distillate, the solvent is reintroduced into contact with said water swollen beads.

8. The method according to claim 6 wherein after removal of the water from the elute, the solvent is reintroduced into contact with said water swollen beads.

9. The method according to claim 5 wherein after removal of the water from the distillate, the phase of the solvent immiscible with water is isolated and reintroduced into contact with said water swollen beads.

10. The method according to claim 6 wherein after removal of the water from the elute, the phase of the solvent immiscible with water is isolated and reintroduced into contact with said water swollen beads.

11. The method according to claim 3 wherein the water-miscible phase of said solvents is selected from the group comprising aliphatic alcohols and ketones with one to three carbon atoms in the molecule, advantageously from ethanol, 2-propanol, and acetone.

12. The method according to claim 3 wherein the said solvents limitedly miscible with water are selected from the group comprising aliphatic alcohols and ketones with four to five carbon atoms in the molecule, advantageously from 1-butanol, 2-butanol, and 2-butanone.

13. The method according to claim 3 wherein the said water-immiscible solvents are selected from the group comprising aromatic hydrocarbons and their derivatives and cycloaliphatic hydrocarbons, advantageously from benzene, toluene, xylene, chlorobenzene, cyclohexane, and methylcyclohexane.

* * * * *